United States Patent
Hunt et al.

(10) Patent No.: US 10,910,104 B2
(45) Date of Patent: *Feb. 2, 2021

(54) SYSTEM AND METHOD FOR UNIFORMLY PRICING ITEMS

(71) Applicant: Medcom Solutions, Inc., Pittsburgh, PA (US)

(72) Inventors: William A. Hunt, Pittsburgh, PA (US); Jennifer Hunt, Pittsburgh, PA (US)

(73) Assignee: Medcom Solutions, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/460,134

(22) Filed: Jul. 2, 2019

(65) Prior Publication Data

US 2019/0325455 A1 Oct. 24, 2019

Related U.S. Application Data

(63) Continuation of application No. 13/315,857, filed on Dec. 9, 2011, now Pat. No. 10,339,532, which is a continuation of application No. 11/836,248, filed on Aug. 9, 2007, now abandoned.

(60) Provisional application No. 60/822,010, filed on Aug. 10, 2006.

(51) Int. Cl.
*G16H 40/20* (2018.01)
*G06Q 10/06* (2012.01)
*G06Q 30/02* (2012.01)
*G06F 19/00* (2018.01)

(52) U.S. Cl.
CPC ........... *G16H 40/20* (2018.01); *G06F 19/328* (2013.01); *G06Q 10/063* (2013.01); *G06Q 30/0283* (2013.01)

(58) Field of Classification Search
None
See application file for complete search history.

(56) References Cited

U.S. PATENT DOCUMENTS

| | | | |
|---|---|---|---|
| 5,018,067 A | 5/1991 | Mohlenbrock et al. |
| 5,325,293 A | 6/1994 | Dorne |
| 5,729,735 A | 3/1998 | Meyering |
| 5,794,220 A | 8/1998 | Hunt |
| 5,852,715 A | 12/1998 | Raz et al. |
| 5,873,069 A | 2/1999 | Reuhl et al. |
| 5,960,407 A | 9/1999 | Vivona |

(Continued)

FOREIGN PATENT DOCUMENTS

| | | |
|---|---|---|
| WO | 0193067 | 12/2001 |
| WO | 0210961 | 2/2002 |
| WO | 2005059685 | 6/2005 |

OTHER PUBLICATIONS

Price Check: The Mystery of Hospital Pricing. Dec. 2005. California Healthcare Foundation (Year: 2005).*

(Continued)

*Primary Examiner* — Scott A Zare
(74) *Attorney, Agent, or Firm* — Leech Tishman Fuscaldo & Lampl; Michael D. Lazzara (57) ABSTRACT

A computer-assisted method for uniformly pricing chargeable items in a healthcare provider's chargeable item database is disclosed. The method applies uniform pricing to identical or related chargeable items. A system for uniformly pricing related chargeable items is also disclosed.

22 Claims, 3 Drawing Sheets

(56) References Cited

U.S. PATENT DOCUMENTS

| | | | |
|---|---|---|---|
| 5,987,425 A | 11/1999 | Hartman et al. | |
| 6,266,655 B1 | 7/2001 | Kalyan | |
| 6,507,822 B1 | 1/2003 | Walker et al. | |
| 6,826,538 B1 | 11/2004 | Kalyan et al. | |
| 6,850,903 B2 | 2/2005 | Levine | |
| 6,910,017 B1 | 6/2005 | Woo et al. | |
| 6,965,867 B1 | 11/2005 | Jameson | |
| 7,010,494 B2 | 3/2006 | Etzioni et al. | |
| 7,020,617 B2 | 3/2006 | Ouimet | |
| 7,062,447 B1 | 6/2006 | Valentine et al. | |
| 7,124,116 B2 * | 10/2006 | Huyler | G06Q 30/02 705/400 |
| 7,346,522 B1 | 3/2008 | Baylor et al. | |
| 7,565,300 B2 | 7/2009 | Hunt et al. | |
| 8,073,709 B2 * | 12/2011 | Moreno | G06Q 10/10 705/2 |
| 8,103,541 B2 | 1/2012 | Abrams | |
| 8,615,403 B2 * | 12/2013 | Lipsky | G16H 40/20 705/2 |
| 2001/0032196 A1 | 10/2001 | Krespi | |
| 2002/0004789 A1 | 1/2002 | Huyler | |
| 2002/0026368 A1 | 2/2002 | Carter | |
| 2002/0046128 A1 | 4/2002 | Abe et al. | |
| 2002/0065717 A1 | 5/2002 | Miller et al. | |
| 2002/0072956 A1 | 6/2002 | Willems et al. | |
| 2002/0073051 A1 | 6/2002 | Blouin et al. | |
| 2002/0095327 A1 | 7/2002 | Zumel et al. | |
| 2002/0099596 A1 | 7/2002 | Geraghty | |
| 2002/0116348 A1 | 8/2002 | Phillips et al. | |
| 2002/0165834 A1 | 11/2002 | Delurgio et al. | |
| 2002/0178109 A1 | 11/2002 | Bye | |
| 2002/0188576 A1 | 12/2002 | Peterson et al. | |
| 2002/0194143 A1 | 12/2002 | Banerjee et al. | |
| 2003/0110066 A1 | 6/2003 | Walser et al. | |
| 2003/0120579 A1 | 6/2003 | Carter, III | |
| 2003/0126097 A1 | 7/2003 | Zhang et al. | |
| 2003/0149709 A1 | 8/2003 | Banks | |
| 2003/0177103 A1 | 9/2003 | Ivanov et al. | |
| 2003/0200185 A1 | 10/2003 | Huerta et al. | |
| 2003/0216946 A1 | 11/2003 | Ferraro | |
| 2003/0217016 A1 | 11/2003 | Pericle | |
| 2003/0229502 A1 | 12/2003 | Woo | |
| 2004/0024715 A1 | 2/2004 | Ouimet | |
| 2004/0049470 A1 | 3/2004 | Ouimet | |
| 2004/0068413 A1 | 4/2004 | Musgrove et al. | |
| 2004/0073520 A1 | 4/2004 | Eskandari | |
| 2004/0128163 A1 | 7/2004 | Goodman et al. | |
| 2004/0128261 A1 | 7/2004 | Olavson et al. | |
| 2004/0199417 A1 | 10/2004 | Baxter et al. | |
| 2004/0205031 A1 | 10/2004 | Cranner | |
| 2004/0243438 A1 | 12/2004 | Mintz | |
| 2004/0249769 A1 | 12/2004 | Mathews et al. | |
| 2004/0267674 A1 | 12/2004 | Feng et al. | |
| 2005/0004819 A1 | 1/2005 | Etzioni et al. | |
| 2005/0071249 A1 | 3/2005 | Nix et al. | |
| 2005/0086181 A1 | 4/2005 | Melzer | |
| 2005/0131810 A1 | 6/2005 | Garrett | |
| 2005/0149381 A1 | 7/2005 | Ravulapati et al. | |
| 2005/0149458 A1 | 7/2005 | Eglen et al. | |
| 2005/0171918 A1 | 8/2005 | Eden et al. | |
| 2005/0197971 A1 | 9/2005 | Kettner et al. | |
| 2005/0256810 A1 | 11/2005 | Lund | |
| 2005/0273415 A1 | 12/2005 | Mathews et al. | |
| 2006/0010082 A1 | 1/2006 | Gee et al. | |
| 2006/0047574 A1 | 3/2006 | Sundaram et al. | |
| 2006/0047608 A1 | 3/2006 | Davis et al. | |
| 2006/0059010 A1 | 3/2006 | Chavis-Smith et al. | |
| 2006/0080265 A1 | 4/2006 | Hinds et al. | |
| 2006/0106678 A1 | 5/2006 | Walker et al. | |
| 2006/0136264 A1 * | 6/2006 | Eaton | G06Q 30/06 705/2 |
| 2007/0067247 A1 | 3/2007 | Brookhart | |
| 2008/0004981 A1 * | 1/2008 | Gopalpur | G06Q 30/0635 705/26.81 |
| 2010/0324928 A1 | 12/2010 | Dang | |
| 2012/0166212 A1 | 6/2012 | Campbell | |
| 2018/0366213 A1 | 12/2018 | Fidone et al. | |
| 2019/0096017 A1 | 3/2019 | Whitley et al. | |

OTHER PUBLICATIONS

Bils et al., "Understanding How Price Responds to Costs and Production," Carnegie-Rochester Conference Series on Public Policy, Jul. 1999.

Breidert, et al., "Reservation Price Estimation by Adaptive Conjoint Analysis".

Gerber, "Price Check: The Mystery of Hospital Pricing", Dec. 2005, California HealthCare Foundation, ISBN 1-933795-00-X.

Dennison, "Hospital Bills Sometimes Confound Even the Experts", Knight-Ridder Tribune Business News, The Montana Standard, Sep. 3, 2006.

* cited by examiner

SYSTEM AND METHOD FOR UNIFORMLY PRICING ITEMS

CROSS REFERENCE TO RELATED APPLICATIONS

This application is a continuation of U.S. patent application Ser. No. 13/315,857 filed on Dec. 9, 2011, which is a continuation of U.S. patent application Ser. No. 11/836,248, filed on Aug. 9, 2007, which claims priority to U.S. Provisional Patent Application No. 60/822,010, filed on Aug. 10, 2006.

BACKGROUND

Computerized methods for reviewing a healthcare provider's chargeable item database are known in the art. However, these methods are often plagued with non-uniform pricing schemes for identical or related chargeable items. Such inconsistent pricing schemes are problematic for the provider in at least three respects. First, pricing errors can affect a provider's proper reimbursement. Second, pricing errors or inconsistent pricing can be a concern in terms of patients' perception as to why the same service within a single healthcare provider is priced differently in different departments within that healthcare provider. Finally, the inconsistent pricing generates inconsistent gross revenue charges which cause irregularities when the healthcare provider files the annual Medicare Cost Report, HCFA-2552 Cost Report. Uniformity of changes is a provision in the Medicare Provider Manual to maintain consistency in the cost to charge ratio for calculations in the Medicare Cost Report, HCFA-2552. Implementing and preserving uniform pricing between departments throughout the healthcare provider is an arduous task.

SUMMARY

In an embodiment, a computer-assisted method for uniformly pricing a group of chargeable items that are each identified by an identifier is disclosed. The method comprises the steps of:
  a. searching, using a processor, a chargeable item database for chargeable items that are identified by said identifier to create said group;
  b. selecting, using said processor, a revenue data set to select a preselected parameter that is used to calculate a uniform price for said chargeable items in said group;
  c. generating, using said processor, said uniform price, wherein said uniform price is generated according to a formula:

$$\text{Uniform Price}(I_{group}) = \text{Charged Price}(I_{preselected\ parameter}),$$

wherein Uniform Price ($I_{group}$) is said generated uniform price for each said chargeable item in said group, and wherein Charged Price ($I_{preselected\ parameter}$) is a price charged for one of said chargeable items in said group that satisfies said preselected parameter; and
  d. repricing, using said processor, a price charged for each said chargeable item in said group according to said formula.

In another embodiment, a uniform pricing system for use by a healthcare provider is disclosed. The system comprises a chargeable item database that stores as data a line-item listing for each of a plurality of chargeable items that are chargeable by said healthcare provider to a patient, wherein said line-item listing for each of said chargeable items includes at least an identifier that identifies said chargeable item. The system also comprises a revenue and usage database that stores as data a revenue data set for one of said chargeable items actually charged to at least one patient by said healthcare provider, wherein said revenue data set includes statistical volume data about said chargeable item that was actually charged. The system also comprises a computer processor configured to execute instructions to:
  i. search said chargeable item database for a plurality of chargeable items that are identified by a same said identifier to form a group;
  ii. derive a preselected parameter from said revenue data set, wherein said preselected parameter is used to calculate a uniform price for said chargeable items in said group;
  iii. generate said uniform price according to a formula: Uniform Price ($I_{group}$)=Charged Price ($I_{preselected\ parameter}$), wherein Uniform Price ($I_{group}$) is said generated uniform price for each said chargeable item in said group, and wherein Charged Price ($I_{preselected\ parameter}$) is a price charged for one of said chargeable items in said group that satisfies said preselected parameter; and
  iv. reprice a price charged for each said chargeable item in said group according to said formula.

In another embodiment, an apparatus for uniformly pricing chargeable items is disclosed. The apparatus comprises means for searching a chargeable item database for chargeable items that are identified by said identifier to create said group. The apparatus also comprises means for selecting a revenue data set to select a preselected parameter that is used to calculate a uniform price for said chargeable items in said group. The apparatus further comprises means for generating said uniform price, wherein said uniform price is generated according to a formula:

$$\text{Uniform Price}(I_{group}) = \text{Charged Price}(I_{preselected\ parameter}),$$

wherein Uniform Price ($I_{group}$) is said generated uniform price for each said chargeable item in said group, and wherein Charged Price ($I_{preselected\ parameter}$) is a price charged for one of said chargeable items in said group that satisfies said preselected parameter. The apparatus further comprises means for repricing a price charged for each said chargeable item in said group according to said formula.

DETAILED DESCRIPTION

In order to properly understand the disclosure of the claimed invention, certain terms used herein are described in the following paragraph. While the inventors describe the following terms, the inventors in no way intend to disclaim the ordinary and accustomed meanings of these terms.

As used herein, "chargeable item" refers to a supply, service, or procedure provided by or on behalf of a healthcare provider that is chargeable to a patient who has received that supply, service, or procedure. Each chargeable item may be designated by a unique procedural code and a unique internal code. In examples, chargeable items are technical chargeable items such as healthcare provider charges for services, procedures, and supplies or professional chargeable items such as physician service charges.

As used herein, "internal code" refers to an alphanumeric identification code that identifies the department within a healthcare provider that offers a chargeable item. The internal code is stored in a healthcare provider's chargeable item database (defined below) on a departmental basis as part of the data for each line item.

As used herein, "procedural code" refers to an alphanumeric identification code that is assigned to a chargeable item and that is stored in a healthcare provider's chargeable item database as part of the data for each line item. In an example, the "procedural code" is "Current Procedural Terminology," also referred to as "CPT®" (CPT® is a registered trademark of the American Medical Association), which is a listing of descriptive terms and identifying codes owned by the American Medical Association for reporting medical services and procedures performed by physicians and hospitals. Current Procedural Terminology is a copyright 2005 American Medical Association. All Rights Reserved. No fee schedules, basic units, relative values, or related listings are included in CPT. The AMA assumes no liability for the data contained therein. Applicable FARS/DFARS restrictions apply to government use. The purpose of the descriptive procedural terminology of CPT is to provide a uniform manner of describing medical surgical and diagnostic services on a national basis. In another example, the procedural code is the HCFA Common Procedure Coding System (HCPCS) codes published by Medicare that are used to designate particular supplies, procedures, or services provided by a healthcare provider. In another example, the procedure code is the International Classification of Diseases codes published by the World Health Organization. In another example, the procedural code is derived from published codes developed by private insurance carriers or HMOs.

As used herein, a "modifier" means an additional alphanumeric code that further identifies the chargeable item described by a procedural code.

As used herein, "related chargeable item" means two or more chargeable items having the same procedural code.

As used herein, "uniformly pricing" refers to a method of consistently pricing related chargeable items offered by a plurality of departments of a healthcare provider in order to achieve consistent billing to patients for related chargeable items across departments.

As used herein, "chargeable item database" 20 also referred to as a "chargemaster" or a "service master," and abbreviated in the figures as "CDM" is a database that stores as data a comprehensive and provider-specific line-item listing of all of the chargeable items that are chargeable by a healthcare provider to a patient. The chargeable item database 20 is stored on a computer-readable storage medium 40 and is coded in a form suitable for processing. Each line-item stored in the chargeable item database 20 contains a plurality of data about the chargeable item to which the line-item relates, including, for example: description, procedural code, price charged, internal code, and any necessary modifiers. An example of data shown in a chargeable item database is shown in Table 1.

TABLE 1

| Internal Code | Description | Procedural Code | Charged Price | Modifier |
|---|---|---|---|---|
| XX:1 | Wrist x-ray, 2 view, Operating Room | 73100 | $85 | |
| XX:2 | Wrist x-ray, 2 view, Emergency Room | 73100 | $75 | |
| XX:3 | Wrist x-ray, 2 view, Radiology | 73100 | $70 | |
| XX:4 | Wrist X-ray, 2 view, Outpatient Clinic | 73100 | $55 | −52 |

Figure 1:
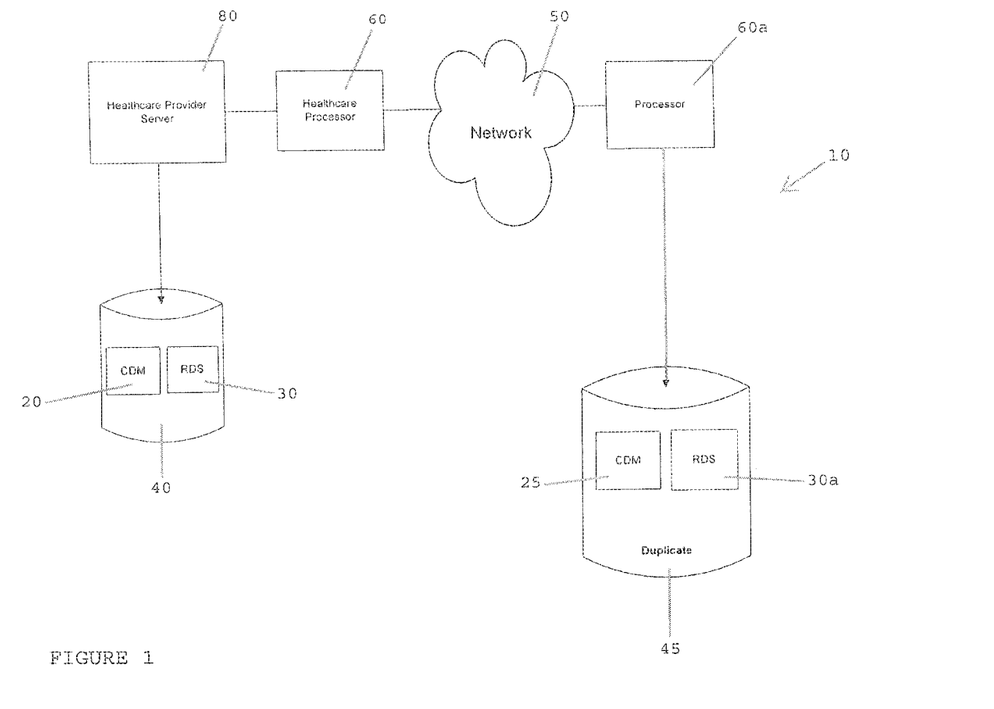
FIG. 1 shows an embodiment of a system for uniformly pricing a chargeable item across departments of a healthcare provider.

As used herein, "revenue and usage database" 30, abbreviated in the figures as "RDS" is a database that stores the same data as is stored in the chargeable item database 20, and that further includes statistical volume data about the total number of units of each chargeable item actually charged to patients by the healthcare provider. In examples, the revenue and usage database 30 includes a data set of sales volume, gross revenue, and pricing for each chargeable item listed in the chargeable item database 20. The revenue data set is capable of being updated. In an example, the revenue data set for each chargeable item is stored in a database 30 that is stored on a computer-readable storage medium and coded in a form suitable for processing. In an example, the storage medium is the storage medium 40 on which the chargeable item database 20 is stored. In another example, the storage medium is a second storage medium 45, as shown in FIG. 1. In an alternate embodiment (not shown), each revenue data set is stored as one of the line-item data entries in the chargeable item database 20. Optionally, the revenue data set 30 is a utilization file created by or for the healthcare provider that is uploaded to one of the computer-readable storage media 40, 45 or to the chargeable item database 20. In an example, the revenue data set is collected at regular time intervals, such as daily, weekly, monthly, quarterly, or annually. The revenue data set for each chargeable item comprises the gross revenue earned by the healthcare provider from sales of the chargeable item, the number of units of the chargeable item sold, or the price charged by the healthcare provider for the chargeable item. In an example, the revenue data set further comprises a predicted price that is the result of either a future price or a budgeted price change. Optionally, the revenue and usage database 30 also records the statistical volume data by whether the patient(s) receiving the chargeable item is an inpatient or an outpatient, and by which payor is responsible for paying the bill for the chargeable item on behalf of each patient. An example of data shown in a revenue and usage database 30 is shown in Table 2 (below).

In an embodiment, a system 10 of uniformly pricing chargeable items provided by a healthcare provider 80 is disclosed. In an example, the system 10 is embodied in a computer system 10 such as the one shown in FIG. 1, which shows an example of a system 10 that comprises at least one processor 60, 60a that uses at least one set of instructions to implement uniform pricing in the chargeable item database 20. The components contained in the computer system of FIG. 1 may be those found in general purpose computer systems and the illustrated components are intended to represent a broad category of such computer components. Various embodiments of the disclosure may be implemented on computer-readable media. The terms "computer-readable medium" and "computer-readable media" in the plural as used herein may include, for example, magnetic and optical memory devices such as diskettes, compact disks of both read-only and writeable varieties, optical disk drives, hard disk drives, etc. A computer-readable medium may also include memory storage that can be physical, virtual, permanent, temporary, semi-permanent, and/or semi-temporary.

In various embodiments the system 10 is implemented in software, and the storage media 40, 45 stores the executable code when in operation. The main memory may include banks of dynamic random-access memory (RAM) as well as high-speed capable memory. In embodiments where the system 10 is a computer system, the processor 60, 60a may contain a single microprocessor, or may contain a plurality of microprocessors for configuring the computer as a multi-processor system.

As described in more detail below, in embodiments of the system 10, the processor 60, 60a uses at least one set of instructions to review the chargeable item database 20 to identify chargeable items having the same procedural code (i.e., related chargeable items). In instances where related chargeable items have different internal codes (such that the chargeable item is offered by a plurality of departments within the healthcare provider) instructions determine if the price charged for each of those related chargeable items offered by the plurality of departments is uniform. Where the price charged is not uniform across departments, the processor 60, 60a uses at least one set of instructions to calculate a uniform final price for the related chargeable items having the same procedural code. The final price is established by using a predetermined parameter, where the predetermined parameter is derived from data stored in a revenue and usage database 30. In an example, uniform pricing is implemented where the instructions set the predetermined parameter to be the highest sales volume, such that the price charged for each related chargeable item is updated in the chargeable item database 20 to equal the price charged for that related chargeable item having the highest sales volume. In another example, uniform pricing is implemented where the instructions set the predetermined parameter to be highest gross revenue, such that the price charged for each related chargeable item is updated in the chargeable item database 20 to equal the price charged for that related chargeable item having the highest gross revenue. In another example, uniform pricing is implemented where the instructions set the predetermined parameter to be the highest price, such that the price charged for each related chargeable item is updated in the chargeable item database 20 to equal the price charged for that related chargeable item having the highest price charged. The instructions require that the price charged for the chargeable item that meets the criteria required by the predetermined parameter is used to update the price charged by other departments for all other related chargeable items to generate uniform pricing for all related chargeable items that are identified by a particular procedural code.

Optionally, one of the data entries for at least one of the related chargeable items is an exclusionary code that flags that chargeable item to be excluded from calculations, updates, and/or uniform pricing. In an example, an item having an exclusionary code is designated by the code "True" or "T" and an item not having an exclusionary code is designated by the code "False" or "F." Reasons for exclusion include but are not limited to: (1) the charged price is manually set by the healthcare provider; (2) there is no sales volume or gross revenue data for the chargeable item; and (3) the healthcare provider has designated that the charged price for the chargeable item is to be maintained at its current price.

The chargeable item database 20 is capable of being updated. Updates include changes to the data entries for chargeable items, including price. Updates may be implemented by a processor 60, 60a that uses a set of computer-coded instructions stored in a computer-readable storage medium 40, 45 to implement the update.

Optionally, the processor 60, 60a uses instructions to generate a report that summarizes the result of the review and reports any calculated final prices or any updates made to the chargeable item database 20. The results of the review request or the search request may be displayed in a format that can be exported to a software-based file such as a Microsoft Excel® file.

Optionally, the system further comprises a duplicate database 25 that is a duplicate of the chargeable item database 20 and that is used to perform the review and update of the chargeable item database 20, as shown in FIG. 1. The processor 60, 60a uses instructions to create the duplicate chargeable item or revenue and usage database 25, 35, respectively, which is stored on one of the storage media 40, 45 and replaces or overwrites any preceding duplicate database stored therein. Following the review, calculations, and updates, if any, the processor 60, 60a then uses instructions to export the final price from the duplicate database 25, 35 to the chargeable item database 20, 30 to implement the changes by updating the charged price for each of the related chargeable items.

In order to display textual and graphical information, the system contains 10 the graphics subsystem and the output display (not shown). In an example, the readable formats are displayed on an output display. The output display may include a cathode ray tube display or a liquid crystal display. The graphics subsystem receives textual and graphical information and processes the converted requested update and corresponding data entry from the duplicate database 25 for display on the output display. A graphical user interface (GUI) designed to collect certain information regarding data entries or chargeable items can be used to facilitate entry of the requested update and the corresponding data entry.

The system 10 may further include a mass storage device, peripheral devices, portable storage medium drives, input control devices, a graphics subsystem, and an output display (not shown). The computer system may be connected through one or more data transport means, such as a network 50. For example, the processor 60, 60a and the main memory may be connected via a local microprocessor bus, and the mass storage device, peripheral devices, portable storage medium drives, and graphics subsystem may be connected via one or more input/output (VO) busses. The mass storage device, which may be implemented with a magnetic disk drive or an optical disk drive, is non-volatile storage device for storing data and instructions for use by the processor. In the software embodiment, the mass storage device stores the information software for loading to the main memory.

The system 10 optionally comprises an input device (not shown) for inputting the requested review. The input device has an input control device that provides a portion of the user interface for a user of the system and an input display.

Examples of the input control device are an alphanumeric keypad for inputting alphanumeric and other information, or a cursor control device such as a mouse, a trackball, a stylus, or cursor direction keys. In order to display textual and graphic information, the computer system 10 contains the graphics subsystem and the input display. Examples of the input display include a cathode ray tube display or a liquid crystal display. The graphics subsystem receives textual and graphical information and processes the submitted input for display on the input display. A graphical user interface (GUI) that is designed to collect certain information regarding chargeable items can be used to facilitate entry or input. The input device is optionally a software or web-based application that enables the authorized user to submit input, including the review request or a search request to search the duplicate database 25, 35.

Figure 2A:
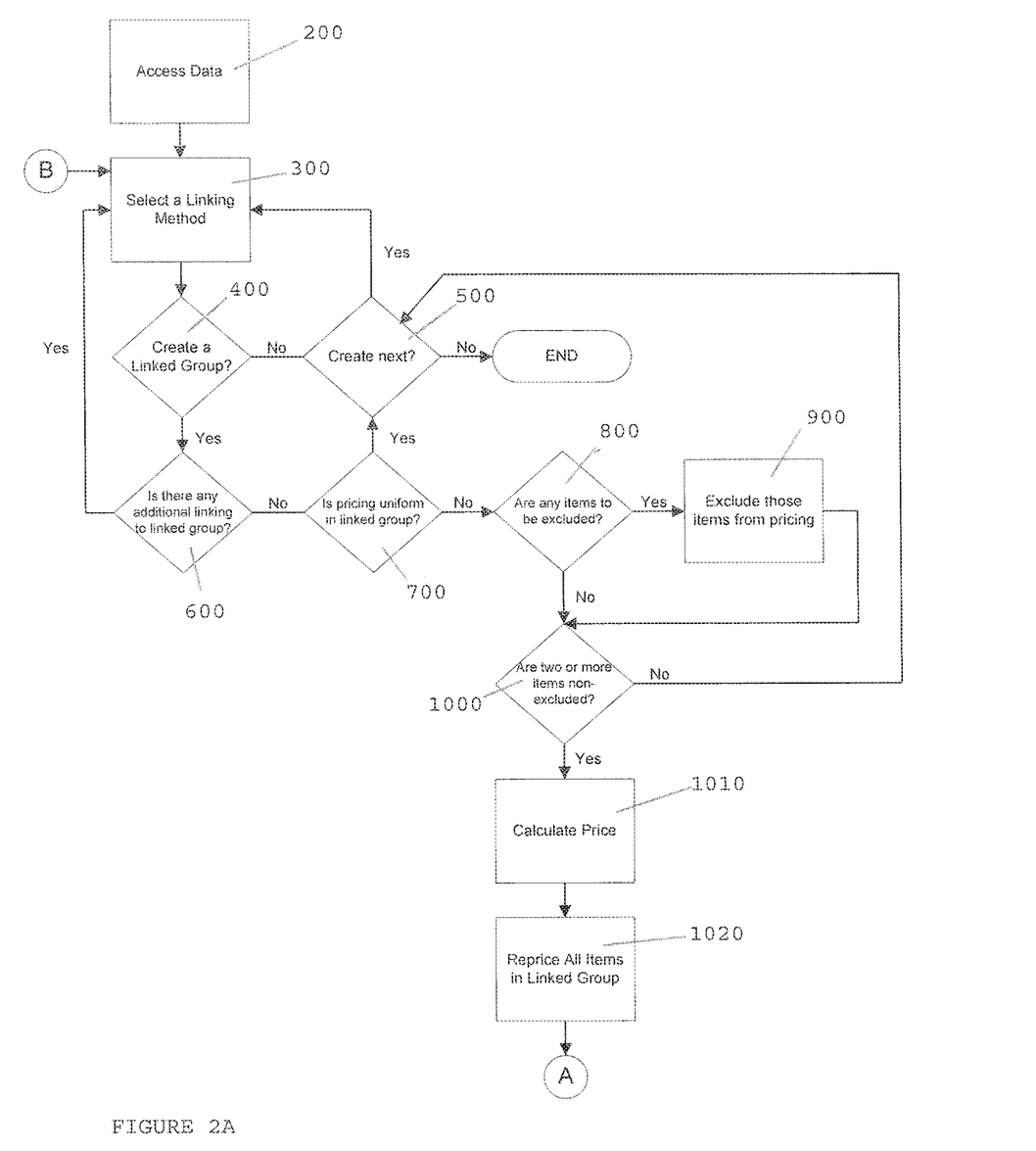
FIGS. 2A and 2B are flowcharts illustrating an embodiment of a method for uniformly pricing a chargeable item across departments of a healthcare provider.
Figure 2B:
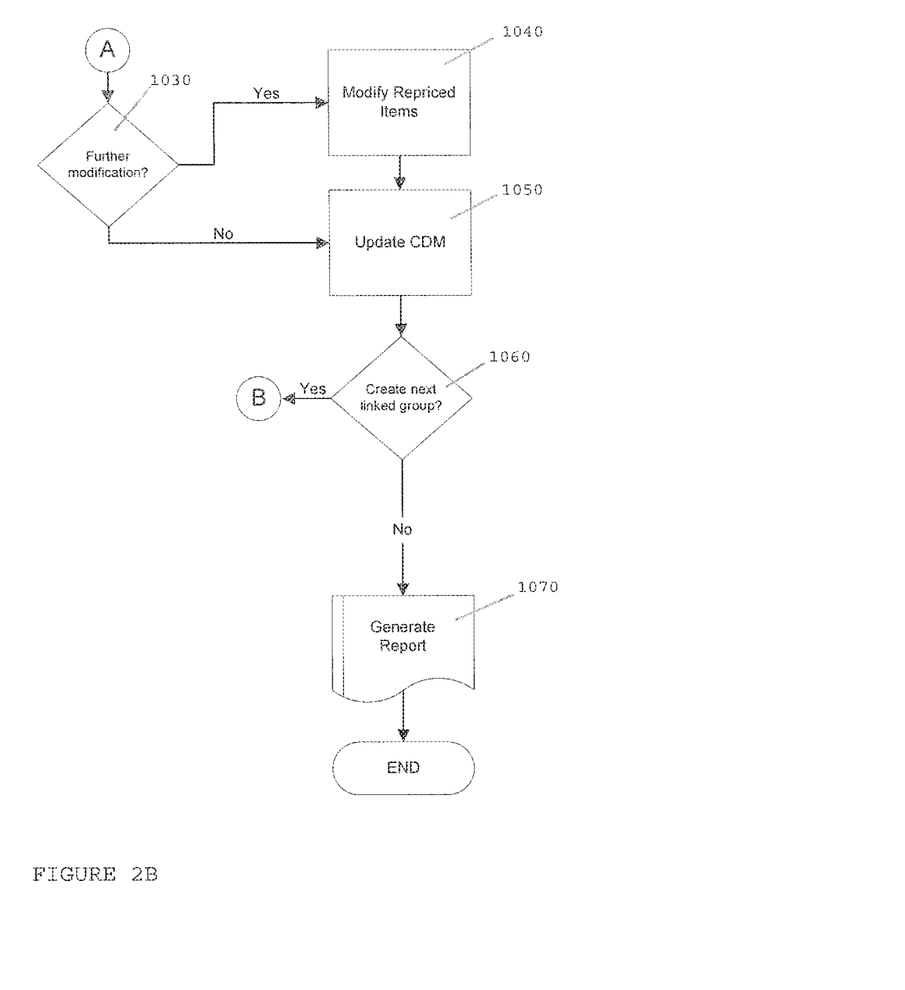

In another embodiment, a computer-implemented method of uniformly pricing items is disclosed. An example of the method of uniform pricing is shown in FIGS. 2A and 2B. The revenue data set is accessed in step 200 and in step 300 a linking method is selected to derive a preselected parameter that is used to calculate the final price for related chargeable items. In an example, the preselected parameter is selected based on business-driven factors that are predetermined by the healthcare provider.

In step 400, the chargeable item database is accessed to create a linked group. In an example a linked group is created by searching the chargeable item database for a selected procedural code to identify related chargeable items, such as by identifying multiple chargeable items in the chargeable item database that have the same procedural code. A linked group is formed where the selected procedural code is entered in the chargeable item database more than one time. All members of a linked group are related chargeable items. If the selected procedural code is not entered in the chargeable item database more than one time, then no further action is required and no updates to the chargeable item database are required, as in step 500, and optionally steps 200 through 400 are repeated for linking on another procedural code.

Optionally, at step 600, the linked group is further defined by narrowing the linked group based on additional linking, such as on another identifier. In an example, the group of chargeable items in the linked group created at step 400 is further narrowed to those chargeable items that include a particular modifier.

At step 700, the method confirms whether the price charged for each chargeable item in the group is uniform. If pricing is uniform, then the method goes back to step 500, described above, to determine if another group should be created. If pricing is not uniform, then the method goes to step 800.

At step 800 the related chargeable items in the linked group are evaluated to determine if any are marked in one of the databases to be excluded from the linking method. Any related chargeable item that is to be excluded from linking is excluded from the calculations in step 900.

At step 1000, it is confirmed that the number of related chargeable items in the linked group is greater than one. If the number of related chargeable items in the linked group is less than or equal to one, then the method repeats step 500, described above.

If the number of related chargeable items in the linked group is greater than one, then at step 1010, the final price for each unexcluded related chargeable item is calculated to be the charged price for the related chargeable item having the preselected parameter derived from the revenue data set in step 200. As described above and as illustrated in an example in Appendix A hereto, the predetermined parameter is the highest sales volume, such that the chargeable item database is updated so that the price charged for each related chargeable item in the linked group is updated to equal the price charged for the related chargeable item having the highest sales volume. In another example, the predetermined parameter is the highest gross revenue, such that the chargeable item database is updated so that the price charged for each related chargeable item is updated to equal the price charged for that related chargeable item having the highest gross revenue. In another example, the predetermined parameter is the highest price, such that the chargeable item database is updated so that the price charged for each related chargeable item is updated to equal the price charged for that related chargeable item having the highest price charged.

At step 1020, all items in the linked group are repriced so that the final price for each related chargeable item is priced as calculated at step 1010 according to the predetermined parameter.

At step 1030, the method asks if further modification to the final price is required. If no, then the method goes to step 1050, at which chargeable item database is updated so that the price charged for each chargeable item in the linked group is equal to the price calculated at step 1010. If yes, then at step 1040, the final price is further modified, and then at step 1050, the chargeable item database is updated so that the price charged for each chargeable item in the linked group is equal to the further modified price calculated at step 1040.

Optionally, at step 1060, the method repeats for another group of related chargeable items.

Optionally, the method further comprises generating a report at step 1070. The report may be generated following any of steps 200-1050 above, although in the example shown in FIG. 2, the report is generated following the step 1060.

EXAMPLES

Table 2 provides the data entries in a revenue and usage database for four chargeable items having item identifiers of: XX:1, XX2, XX:3, and XX:4 and the corresponding revenue data set for each. Related chargeable items XX:1-XX:4 have the same procedural code 73100. Item XX:4 is designated with an exclusionary code "T," to exclude Item XX:4 from all linking calculations. Therefore, any price updates to related chargeable items having procedural code 73100 will not be implemented for Item XX:4 and the charged price will remain $55.

Table 2 also provides the revenue data set for each chargeable item XX:1-XX:4. In the examples below, the predetermined parameter is selected from these data sets to calculate the final price to update the price charged for each unexcluded related chargeable item: X:X1-XX:3. The examples below illustrate the use of a variety of predetermined parameters for the calculations.

TABLE 2

| Internal Code | Description | Procedural Code | Exclusionary Code | Charged Price | Sales Volume | Gross Revenue |
|---|---|---|---|---|---|---|
| X:X1 | Wrist x-ray, 2 view, Operating Room | 73100 | F | $85 | 110 | $9350 |

TABLE 2-continued

| Internal Code | Description | Procedural Code | Exclusionary Code | Charged Price | Sales Volume | Gross Revenue |
|---|---|---|---|---|---|---|
| XX2 | Wrist x-ray, 2 view, Emergency Room | 73100 | F | $75 | 50 | $3750 |
| XX:3 | Wrist x-ray, 2 view, Radiology | 73100 | F | $70 | 205 | $13325 |
| XX:4 | Wrist x-ray, 2 view, Outpatient Clinic | 73100 | T | $55 | 275 | $15125 |

Example 1

In this example, the instructions instruct that the final price of the related chargeable items equals the charge price of the related chargeable item having the highest gross revenue. The instructions utilize the equation set forth in Appendix A attached hereto to compare the gross revenue of each of items X:X1-XX:3. Then, the final price is calculated to equal the charged price of the chargeable item having the highest gross revenue. In this example, the gross revenue of item XX:3, $13325, is greater than the gross revenue of either Item: X:X1 or XX:2. Therefore, the final price for Items: X:X1-XX:3 is calculated by the instructions to equal the charge price of Item XX:3, $65. This is depicted in Table 3, below. As described above, the final price for Item XX:4 is not updated because of the exclusionary code.

TABLE 3

| Internal Code | Description | Procedural Code | Exclusionary Code | Charged Price | Gross Revenue | Final Price |
|---|---|---|---|---|---|---|
| XX:1 | Wrist x-ray, 2 view, Operating Room | 73100 | F | $85 | $9350 | $70 |
| XX:2 | Wrist x-ray, 2 view, Emergency Room | 73100 | F | $75 | $3750 | $70 |
| XX:3 | Wrist x-ray, 2 view, Radiology | 73100 | F | $70 | $13325 | $70 |
| XX:4 | Wrist X-ray, 2 view, Outpatient Clinic | 73100 | T | $55 | $15125 | $55 |

Example 2

In this example, the instructions instruct that the final price of the related chargeable items equal the charge price of the related chargeable item having the highest charge price. The instructions utilize the equation set forth in Appendix A attached hereto to compare the reference of each of items XX:1-XX:3. Then, the final price is calculated to equal the charge price of the chargeable item having the highest charge price. In this example, the charge price of Item XX:1, $85, is greater than the charge price of either Item XX:2 or XX:3. Therefore, the final price for Items XX:1-XX:3 is calculated by the instructions to equal the charge price of item XX:1, $85. This is depicted in Table 4, below. As described above, the final price for Item XX:4 is not updated because of the exclusionary code.

TABLE 4

| Internal Code | Description | Procedural Code | Exclusionary Code | Charged Price | Gross Revenue | Final Price |
|---|---|---|---|---|---|---|
| XX:1 | Wrist x-ray, 2 view, Operating Room | 73100 | F | $85 | $9350 | $85 |
| XX:2 | Wrist x-ray, 2 view, Emergency Room | 73100 | F | $75 | $3750 | $85 |
| XX:3 | Wrist x-ray, 2 view, Radiology | 73100 | F | $70 | $13325 | $85 |
| XX:4 | Wrist x-ray, 2 view, Outpatient Clinic | 73100 | T | $55 | $15125 | $55 |

Example 3

In this example, the instructions instruct that the final price of the related chargeable items equal the charge price of the related chargeable item having the lowest sales volume. The instructions utilize the equation set forth in Appendix A attached hereto to compare the sales of each of items XX:1-XX:3. Then, the final price is calculated to equal the charge price of the chargeable item having the lowest sales volume. In this example, the sales volume of Item XX2, 50, is less than the sales volume of either Item XX:1 or XX:3. Therefore, the final price for Items XX:1-XX:3 is calculated by the instructions to equal the charge price of item XX:2, $75. This is depicted in Table 5, below. As described above, the final price for Item XX:4 is not updated because of the exclusionary code.

TABLE 5

| Internal code | Description | Procedural Code | Exclusionary Code | Charged Price | Sales Volume | Final Price |
|---|---|---|---|---|---|---|
| XX:1 | Wrist x-ray, 2 view, Operating Room | 73100 | F | $85 | 110 | $75 |
| XX:2 | Wrist x-ray, 2 view, Emergency Room | 73100 | F | $75 | 50 | $75 |
| XX:3 | Wrist x-ray, 2 view, Radiology | 73100 | F | $70 | 205 | $75 |

TABLE 5-continued

| Internal code | Description | Procedural Code | Exclusionary Code | Charged Price | Sales Volume | Final Price |
|---|---|---|---|---|---|---|
| XX:4 | Wrist x-ray, 2 view, Outpatient Clinic | 73100 | T | $55 | 275 | $55 |

APPENDIX A. "PC" is Procedural code of interest. "In" is Items having PC, where n=1 . . . n. "CPn" is Charged price for item n. "N" is Number of items having PC, N=n. "PRn" is Reference price for item n. "FP" is Final Price. "Vn" is Sales Volume for item n. GP is Group assigned where all In's where the PC of all items is the same. "GRn" is Gross revenue for item n. "E" is "T" (exclude) or "F" (don't exclude). "P" is preselected parameter, where P is "Pv" (volume), "Pgr" (gross revenue "Prp" (reference price).

STEP ONE. The first step is to identify within the Revenue Data Set all occurrences whereas there are multiple instances of chargeable items that contain identical Procedure Codes. If there are any instances of multiple Procedure Codes, the method then goes to STEP TWO.

STEP TWO. STEP TWO goes to the Revenue Data Set to determine if any of the chargeable items with identical procedure codes have an Exclusionary Flag. Excluded is a characteristic assigned in the chargeable item database and is denoted by a "True" or "T" designation in the chargeable item database. If a chargeable item is not excluded, it is denoted by a "False" or "F" designation in the chargeable item database. If an item is excluded, it is denoted by a "True" or "T" designation. Any excluded item is excluded from further analysis and calculation and FP=CP.

STEP THREE. STEP THREE allows the user to make a selection to identify the PRESELECTED CRITERION under which the chargeable items that contain identical Procedure Codes will be commonly priced such as the highest volume or lowest price.

STEP FOUR. STEP FOUR is where the calculation takes place to determine what price will be used to commonly price all non-excluded chargeable items as follows:

EXAMPLE No. 1: Highest Price–From In in GP find MAX (PRn), for all In GP, set FP=MAX (PRn).

EXAMPLE No. 2: Lowest Price–From In in GP find MIN (PRn); for all In GP, set FP=MIN (PRn).

EXAMPLE No. 3: Highest Gross Revenue–From In in GP find MAX (GRn); for all In GP, set FP=MAX (GRn).

EXAMPLE No. 4: Lowest Gross Revenue–From In in GP find MIN (GRn); for all In GP, set FP=MIN (GRn).

EXAMPLE No. 5: Highest Volume–From In in GP find MAX (Vn); for all In GP, set FP=MAX (Vn).

EXAMPLE No. 6: Lowest Volume–From In in GP find MIN (Vn); for all in GP, set FP=MIN (Vn).

In one embodiment, a computer-assisted method is provided for uniformly pricing chargeable items. The method comprises the steps of: (a) accessing a revenue data set for each chargeable item, each revenue data set comprising at least one of a gross revenue, a sales volume, and a reference price; (b) accessing the healthcare provider's chargeable item database, the chargeable item database storing a plurality of data entries for each chargeable item, the data entries comprising an identifier that uniquely identifies the chargeable item, a charged price, and a procedural code derived from a coding system that assigns the same procedural code to related chargeable items; and (c) reviewing the charged price for the related chargeable item, the step of reviewing comprising at least one of the following: calculating a final price for each of the related chargeable items, the final price equaling the reference price for the related chargeable item having a preselected parameter, the preselected parameter being derived from the revenue data set; or excluding from the calculation any of the related chargeable items having an exclusionary code as one of the data entries.

The method may further comprise the step of calculating a predicted price. In the method, the preselected parameter may be selected from the group consisting of a highest reference price; a highest gross revenue, a highest sale volume, a lowest reference price, a lowest gross revenue, a lowest sale volume, a mean reference price a mean gross revenue, a mean sale volume, a median reference price, a median gross revenue, a median sale volume, a reference price falling within a percentile, a gross revenue falling within the percentile, and a sale volume falling within the percentile. The preselected parameter may be a reference price; a gross revenue, or a sale volume. The reference price may be the charged price or the predicted price.

The method may further comprise a duplicate database, the duplicate database being a duplicate of the chargeable item database, the duplicate database being stored in one of the storage media and capable of being updated. The step of calculating may be performed in the duplicate database. The method may further comprise the step of updating the chargeable item database such that the charged price for each of the related chargeable items equals the calculated final price. The method may further comprise the steps of: (a) updating the duplicate chargeable item database such that the charged price for each of the related chargeable items equals the calculated final price; and (b) uploading the updates to the chargeable item database.

In the method, the chargeable item database may be a Chargemaster, a product list, or a Service Master.

In the method, the procedural code may be selected from the group consisting of a Current Procedural Terminology code, a HCFA Common Procedure Coding System code, an International Classification of Disease code, an internal code, or a private insurer's code. The procedural code may be a Current Procedural Terminology code, a HCFA Common Procedure Coding System code, or an International Classification of Diseases code.

In another aspect, the method further comprises the step of creating the revenue data set.

In certain aspects, a uniform pricing system is provided for use by a healthcare provider. The system may comprise for each chargeable item in the healthcare provider's chargeable item database, a revenue data set comprising at least one of a gross revenue, a sales volume, and a reference price, the revenue data sets for related chargeable items being used to derive a preselected parameter, wherein the chargeable item database stores a plurality of data entries for the chargeable item, the data entries comprising an identifier that uniquely identifies the chargeable item, a charged price for the chargeable item, and a procedural code derived from a coding system that assigns the same procedural code to related chargeable items. In addition, the system may comprise a processor configured to review the charged price for the related chargeable item, the review comprising at least one of the following: calculating a final price for each of the related chargeable items, the final price equaling the reference price for the related chargeable item having the preselected parameter; or excluding from the calculation any of the related chargeable items having an exclusionary code as one of the data entries.

In the system, the preselected parameter may be selected from the group consisting of a highest reference price, a highest gross revenue, a highest sale volume, a lowest reference price, a lowest gross revenue, a lowest sale volume, a mean reference price a mean gross revenue, a mean sale volume, a median reference price, a median gross revenue, a median sale volume, a reference price falling within a percentile, a gross revenue falling within the percentile, and a sale volume falling within the percentile. The preselected parameter may be a highest reference price, a highest gross revenue, or a highest sale volume. The reference price may be the charged price or a predicted price.

The system may further comprise a duplicate database, the duplicate database being a duplicate of the chargeable item database, the duplicate database being stored in one of the storage media and capable of being updated. The chargeable item database may be a Chargemaster, a product list, or a Service Master. The procedural code may be selected from the group consisting of a Current Procedural Terminology code, a HCFA Common Procedure Coding System code, an International Classification of Disease code, an internal code, and a private insurer's code. The procedural code may be a Current Procedural Terminology code, a HCFA Common Procedure Coding System code, or an International Classification of Diseases code.

In one aspect of the system, at least one of the data entries is an exclusionary code that excludes the chargeable item from the calculations.

In other embodiments, an apparatus is provided for uniformly pricing chargeable items. The apparatus may comprise: (a) means for accessing a revenue data set for each chargeable item to derive a preselected parameter, the revenue data set comprising at least one of a gross revenue, a number of units sold, and a reference price; (b) means for accessing a healthcare provider's chargeable item database, the chargeable item database storing a plurality of data entries for the chargeable item, the data entries comprising an identifier that uniquely identifies the chargeable item, a charged price, and a procedural code derived from a coding system that assigns the same procedural code to related chargeable items; and (c) means for reviewing the charged price for the related chargeable item, the means for reviewing comprising at least one of the following: means for calculating a final price for each of the related chargeable items, the final price equaling the reference price for the related chargeable item having the preselected parameter; or means for excluding from the calculation any of the related chargeable items having an exclusionary code as one of the data entries.

In the apparatus, the preselected parameter may be at least one of reference price; gross revenue, sale volume, charged price, or a predicted price. The procedural code may be at least one of a Current Procedural Terminology code, a HCFA Common Procedure Coding System code, or an International Classification of Diseases code.

In certain aspects, a computer readable medium is provided having stored therein instructions which, when executed by a processor, cause the processor to: (a) access a chargeable item database that stores a plurality of data entries for a plurality of the chargeable items, the data entries comprising an identifier that uniquely identifies the chargeable item, a charged price, and a procedural code derived from a coding system that assigns the same procedural code to related chargeable items; (b) identify all related chargeable items having a selected procedural code; (c) access a revenue data set for each of the related chargeable items, the revenue data set comprising at least one of a gross revenue, a sales volume, and a reference price; and (d) review the charged price for the related chargeable item, the instructions for the review comprising at least one of the following: calculating a final price for each of the related chargeable items, the final price equaling the reference price for the related chargeable item having a preselected parameter, the preselected parameter being derived from the revenue data set; or excluding from the calculation any of the related chargeable items having an exclusionary code as one of the data entries.

In the computer readable medium, the preselected parameter may be at least one of reference price, gross revenue, sale volume, charged price, or a predicted price. The procedural code may be at least one of a Current Procedural Terminology code, a HCFA. Common Procedure Coding System code, or an International Classification of Diseases code.

While embodiments of the invention have been shown and described with particularity in connection with the accompanying drawings, the invention may be otherwise embodied within the scope of the following claims.

APPENDIX A

PC Procedural code of interest
$I_n$ Items having PC, where n=1 . . . n
$CP_n$ Charged price for item n
N Number of items having PC, N=n
EFP Final Price
$V_n$ Sales Volume for item n
GP Group of related chargeable items (i.e., each $I_n$ has same PC)
$GR_n$ Gross revenue for item n
E T (exclude) or F (don't exclude)
P preselected parameter, where P is $P_v$ (volume), $P_{gr}$ (gross revenue), $CP_n$ (charge price)

Step One:
The first step is to identify within the Revenue Data Set all occurrences whereas there are multiple instances of chargeable items that contain identical Procedure Codes. If there are any instances of multiple Procedure Codes, the method then goes to STEP TWO.
Is N>1? (where N is the number of items having PC)

Step Two:
STEP TWO goes to the Revenue Data Set to determine if any of the chargeable items with identical procedure codes have an Exclusionary Flag. Excluded is a characteristic assigned in the chargeable item database and is denoted by a "True" or "T" designation in the chargeable item database. If a chargeable item is not excluded, it is denoted by a "False" or "F" designation in the chargeable item database. If an item is excluded, it is denoted by a "True" or "T" designation. Any excluded item is considered separately for further analysis and calculation.
If N>1, then for each item 1 to n, does E=T or E=F?
If E=T for any item $I_n$, then FP for $I_n$=$CP_n$.

Step Three:
STEP THREE allows the user to make a selection to identify the PRESELECTED CRITERION under which the chargeable items that contain identical Procedure Codes will be commonly priced such as the highest volume or lowest price.

Step Four:
STEP FOUR is where the calculation takes place to determine what price will be used to commonly price all non-excluded chargeable items as follows:

Example No. 1: Highest Price

From $I_n$ in GP find MAX ($CP_n$); for all $I_n$ GP, set FP=MAX ($CP_n$)

Example No. 2: Lowest Price

From $I_n$ in GP find MIN ($CP_n$); for all $I_n$ GP, set FP=MIN ($CP_n$)

Example No. 3: Highest Gross Revenue

From $I_n$ in GP find MAX ($GR_n$); for all $I_n$ GP, set FP=MAX ($GR_n$)

Example No. 4: Lowest Gross Revenue

From $I_n$ in GP find MIN ($GR_n$); for all $I_n$ GP, set FP=MIN ($GR_n$)

Example No. 5: Highest Volume

From $I_n$ in GP find MAX ($V_n$); for all $I_n$ GP, set FP=MAX ($V_n$)

Example No. 6: Lowest Volume

From $I_n$ in GP find MIN ($V_n$); for all $I_n$ GP, set FP=MIN ($V_n$)

What is claimed is:

1. A computer-implemented method of uniformly pricing items, the method comprising:
   creating in a first computing environment, with an electronic computer processor, a duplicate of an original electronic chargeable item database located in a second computing environment independent of the first computing environment;
   accessing, by the processor and in an electronic revenue and usage database, a revenue data set comprising data associated with each chargeable item stored in the duplicate electronic chargeable database;
   using computer-implemented instructions executed by the processor for:
      identifying in the duplicate electronic chargeable item database two or more chargeable items having the same procedural code;
      linking the identified chargeable items having the same procedural code in at least one group of related chargeable items;
      selecting a predetermined parameter from the revenue data set stored in the revenue and usage database, the predetermined parameter comprising a comparatively lowest price for selecting from among the respective prices of each item in the linked group of related chargeable items;
      determining, by the processor, a uniform price for the linked group of related chargeable items using the selected predetermined parameter;
      updating in the duplicate chargeable item database, by the processor, price charged data for each item in the linked group of related chargeable items with the determined uniform price; and,
      exporting, by the processor; data from the duplicate chargeable item database to the original chargeable item database for implementing updates or changes derived from the duplicate chargeable item database.

2. The method of claim 1, further comprising excluding from the linked group, using the processor, an excluded chargeable item following creating the linked group of related chargeable items.

3. The method of claim 1, wherein the revenue data set comprises a utilization file associated with a healthcare provider.

4. The method of claim 1, wherein the revenue data set farther comprises at least one predicted price resulting from either a future price or a budgeted price change.

5. The method of claim 1, further comprising associating, using the processor; at least one chargeable item with: an inpatient or outpatient indication, or a payor indication.

6. A computer system programmed for uniformly pricing items, the system comprising:
   an original electronic chargeable item database in a first computing environment;
   a duplicate of the original electronic chargeable item database in a second computing environment independent of a second computing environment of the original electronic chargeable item database;
   an electronic revenue and usage database comprising a revenue data set comprising data associated with each chargeable item stored in the duplicate electronic chargeable database;
   an electronic computer processor programmed for executing computer-implemented instructions for:
      identifying in the duplicate electronic chargeable item database two or more chargeable items having the same procedural code;
      linking the identified chargeable items having the same procedural code in at least one group of related chargeable items;
      selecting a predetermined parameter from the revenue data set stored in the revenue and usage database, the predetermined parameter comprising a comparatively lowest price for selecting from among the respective prices of each item in the linked group of related chargeable items;
      determining a uniform price for the linked group of related chargeable items using the selected predetermined parameter;
      updating in the duplicate chargeable item database price charged data for each item in the linked group of related chargeable items with the determined uniform price; and,
      exporting data from the duplicate chargeable item database to the original chargeable item database for implementing updates or changes derived from the duplicate chargeable item database.

7. The system of claim 6, farther comprising the processor programmed for excluding from the linked group an excluded chargeable item following creating the linked group of related chargeable items.

8. The system of claim 6, wherein the revenue data set comprises a utilization file associated with a healthcare provider.

9. The system of claim 6, wherein the revenue data set farther comprises at least one predicted price resulting from either a future price or a budgeted price change.

10. The system of claim 6, further comprising the processor programmed for associating at least one chargeable item with:
    an inpatient or outpatient indication, or
    a payor indication.

11. A computer-implemented method of uniformly pricing items, the method comprising:

creating in a first computing environment, with an electronic computer processor, a duplicate of an original electronic chargeable item database located in a second computing environment independent of the first computing environment;
accessing, by the processor and in an electronic revenue and usage database, a revenue data set comprising data associated with each chargeable item stored in the duplicate electronic chargeable database;
using computer-implemented instructions executed by the processor for:
identifying in the duplicate electronic chargeable item database two or more chargeable items having the same procedural code;
linking the identified chargeable items having the same procedural code in at least one group of related chargeable items;
selecting a predetermined parameter from the revenue data set stored in the revenue and usage database; the predetermined parameter comprising a mean price for selecting from among the respective prices of each item in the linked group of related chargeable items;
determining, by the processor, a uniform price for the linked group of related chargeable items using the selected predetermined parameter;
updating in the duplicate chargeable item database, by the processor, price charged data for each item in the linked group of related chargeable items with the determined uniform price; and,
exporting, by the processor, data from the duplicate chargeable item database to the original chargeable item database for implementing updates or changes derived from the duplicate chargeable item database.

12. The method of claim 11, further comprising the processor programmed for excluding from the linked group an excluded chargeable item following creating the linked group of related chargeable items.

13. The method of claim 11, wherein the revenue data set comprises a utilization file associated with a healthcare provider.

14. The method of claim 11, wherein the revenue data set further comprises at least one predicted price resulting from either a future price or a budgeted price change.

15. A computer-implemented method of uniformly pricing items, the method comprising:
creating in a first computing environment, with an electronic computer processor, a duplicate of an original electronic chargeable item database located in a second computing environment independent of the first computing environment;
accessing, by the processor and in an electronic revenue and usage database, a revenue data set comprising data associated with each chargeable item stored in the duplicate electronic chargeable database;
using computer-implemented instructions executed by the processor for:
identifying in the duplicate electronic chargeable item database two or more chargeable items having the same procedural code;
linking the identified chargeable items having the same procedural code in at least one group of related chargeable items;
selecting a predetermined parameter from the revenue data set stored in the revenue and usage database, the predetermined parameter comprising a median price for selecting from among the respective prices of each item in the linked group of related chargeable items;
determining, by the processor, a uniform price for the linked group of related chargeable items using the selected predetermined parameter;
updating in the duplicate chargeable item database, by the processor, price charged data for each item in the linked group of related chargeable items with the determined uniform price; and,
exporting, by the processor, data from the duplicate chargeable item database to the original chargeable item database for implementing updates or changes derived from the duplicate chargeable item database.

16. The method of claim 15, further comprising the processor programmed for excluding from the linked group an excluded chargeable item following creating the linked group of related chargeable items.

17. The method of claim 15, wherein the revenue data set comprises a utilization file associated with a healthcare provider.

18. The method of claim 15, wherein the revenue data set further comprises at least one predicted price resulting from either a future price or a budgeted price change.

19. A computer-implemented method of uniformly pricing items, the method comprising:
creating in a first computing environment, with an electronic computer processor, a duplicate of an original electronic chargeable item database located in a second computing environment independent of the first computing environment;
accessing, by the processor and in an electronic revenue and usage database, a revenue data set comprising data associated with each chargeable item stored in the duplicate electronic chargeable database;
using computer-implemented instructions executed by the processor for:
identifying in the duplicate electronic chargeable item database two or more chargeable items having the same procedural code;
linking the identified chargeable items having the same procedural code in at least one group of related chargeable items;
selecting a predetermined parameter from the revenue data set stored in the revenue and usage database, the predetermined parameter comprising a price falling within a predetermined percentile for selecting from among the respective prices of each item in the linked group of related chargeable items;
determining, by the processor, a uniform price for the linked group of related chargeable items using the selected predetermined parameter;
updating in the duplicate chargeable item database, by the processor, price charged data for each in the linked group of related chargeable items with the determined uniform price; and,
exporting, by the processor, data from the duplicate chargeable item database to the original chargeable item database for implementing updates or changes derived from the duplicate chargeable item database.

20. The method of claim 19, further comprising the processor programmed for excluding from the linked group an excluded chargeable item following creating the linked group of related chargeable items.

21. The method of claim 19, wherein the revenue data set comprises a utilization file associated with a healthcare provider.

22. The method of claim 19, wherein the revenue data set further comprises at least one predicted price resulting from either a future price or a budgeted price change.

* * * * *